(12) United States Patent
Franzi et al.

(10) Patent No.: US 10,970,978 B2
(45) Date of Patent: Apr. 6, 2021

(54) METHOD FOR THE BROADCASTING, BY A WATCH, OF AN INFORMATIVE MESSAGE RELATING TO AN EVALUATION OF THE QUALITY OF LIFE OF A WEARER OF SAID WATCH

(71) Applicant: Tissot SA, Le Locle (CH)

(72) Inventors: Edoardo Franzi, Cheseaux-Noreaz (CH); Andrea Dunbar, St-Blaise (CH); Engin Turetken, Ecublens (CH); Virginie Moser, Diesse (CH); Patrick Stadelmann, Boudry (CH); Lingchuan Zhou, Marin-Epagnier (CH)

(73) Assignee: Tissot SA, Le Locle (CH)

( * ) Notice: Subject to any disclaimer, the term of this patent is extended or adjusted under 35 U.S.C. 154(b) by 0 days.

(21) Appl. No.: 16/596,899

(22) Filed: Oct. 9, 2019

(65) Prior Publication Data

US 2020/0134991 A1    Apr. 30, 2020

(30) Foreign Application Priority Data

Oct. 26, 2018    (EP) ..................... 18202778

(51) Int. Cl.
  *G08B 7/06*    (2006.01)
  *G08B 23/00*   (2006.01)
  *G08B 29/02*   (2006.01)
(52) U.S. Cl.
  CPC .............. *G08B 7/06* (2013.01); *G08B 23/00* (2013.01)
(58) Field of Classification Search
  CPC .................................................. A61B 5/0402
  See application file for complete search history.

(56) References Cited

U.S. PATENT DOCUMENTS 7,261,690 B2     8/2007   Teller et al.
2008/0262364 A1  10/2008  Aarts
(Continued)

FOREIGN PATENT DOCUMENTS

CN    104133366 A    11/2014
CN    204440023 U    7/2015
(Continued)

OTHER PUBLICATIONS

European Search Report dated Mar. 28, 2019 in European Application 18202778.9 filed on Oct. 26, 2018 (with English Translation of Categories of Cited Documents).
(Continued)

*Primary Examiner* — Joseph H Feild
*Assistant Examiner* — Pameshanand Mahase
(74) *Attorney, Agent, or Firm* — Oblon, McClelland, Maier & Neustadt, L.L.P.

(57) ABSTRACT

A method for the broadcasting by a watch of an informative message relating to an evaluation of the quality of life of a wearer of the watch includes the following steps: recording, by the processing unit, of data describing at least one factual episode of at least one type of environmental event recorded during a given period; identifying at least one type of environmental event disturbing the quality of life of the wearer from processing of the descriptive data; estimating an evaluation index of the quality of life of the wearer according to an indicator of disturbance of the quality of life relating to each type of environmental event disturbing the quality of life identified, and design of the informative message including the estimated evaluation index in prediction of its broadcasting to the wearer.

9 Claims, 1 Drawing Sheet

(56) References Cited

U.S. PATENT DOCUMENTS

| | | | |
|---|---|---|---|
| 2009/0128487 A1 | 5/2009 | Langereis et al. | |
| 2011/0245633 A1* | 10/2011 | Goldberg | A61B 5/165 |
| | | | 600/301 |
| 2014/0135592 A1 | 5/2014 | Ohnemus et al. | |
| 2015/0347711 A1* | 12/2015 | Soli | H04M 1/72538 |
| | | | 705/3 |
| 2016/0019360 A1* | 1/2016 | Pahwa | G16H 10/60 |
| | | | 705/3 |
| 2016/0058336 A1* | 3/2016 | Blahnik | A61B 5/7435 |
| | | | 600/595 |
| 2016/0246259 A1 | 8/2016 | Zhang | |
| 2019/0373320 A1* | 12/2019 | Balsamo | H04N 21/485 |

FOREIGN PATENT DOCUMENTS

| | | |
|---|---|---|
| JP | 2004-503283 A | 2/2004 |
| JP | 2014-032572 A | 2/2014 |
| RU | 126484 U | 3/2013 |
| WO | WO 2007/107900 A2 | 9/2007 |
| WO | WO 2011/109716 A2 | 9/2011 |
| WO | 2015/107745 | 7/2015 |

OTHER PUBLICATIONS

Office Action dated Oct. 25, 2019, in corresponding Russian application No. 2019134177/28 with English translation.
Notice of the Reasons for Refusal dated Sep. 15, 2020, in corresponding application No. JP 2019-193214, with English translation.
Notice of Grounds for Rejection dated Jan. 10, 2021, in corresponding Korean Patent Application No. 10-2019-0134131 (with English translation).

* cited by examiner

METHOD FOR THE BROADCASTING, BY A WATCH, OF AN INFORMATIVE MESSAGE RELATING TO AN EVALUATION OF THE QUALITY OF LIFE OF A WEARER OF SAID WATCH

CROSS-REFERENCE TO RELATED APPLICATION

This application claims priority to European Patent Application No. 18202778.9 filed on Oct. 26, 2018, the entire disclosure of which is hereby incorporated herein by reference.

TECHNICAL FIELD

The present invention relates to a method for the broadcasting, by a watch, of an informative message relating to an evaluation of the quality of life of a wearer of said watch and a system implementing such a method. The invention also relates to a watch comprising such a system as well as a computer program.

PRIOR ART

The variation in the quality of life of an individual has an impact on various states thereof such as the physical state, the psychological state or the somatic state. In such a context, it is therefore understood that it is important to be able to evaluate this quality of life of an individual in order in particular to be able where applicable to improve it.

To do this, methods are known in the prior art making provision for carrying out an evaluation of quality of life using a data processing of measurements generally coming from activity monitoring sensors or physiological sensors.

However, one of the major drawbacks of such methods is related to the fact that the evaluation of the quality of life proposed is often imprecise or even erroneous because it is carried out from measurement data that are sometimes difficult to obtain and which are not always in direct relationship with conditions related to quality of life.

It is understood that there exists a need to find an alternative solution, in particular that does not have the drawbacks of the prior art.

SUMMARY OF THE INVENTION

One aim of the present invention is consequently to propose a method for the broadcasting, by a watch, of an informative message relating to an evaluation of quality of life that is reliable and simple to implement.

For this purpose, the invention relates to a method for the broadcasting by a watch of an informative message relating to an evaluation of the quality of life of a wearer of said watch, the method comprising the following steps:
  recording (10), by the processing unit (2), of data describing at least one factual episode of at least one type of environmental event recorded during a given period;
  identification (11) of at least one type of environmental event disturbing the quality of life of the wearer from processing of said descriptive data;
  estimation (16) of an evaluation index of the quality of life of the wearer according to an indicator of disturbance of the quality of life relating to each type of environmental event disturbing the quality of life identified, and design (17) of the informative message comprising the estimated evaluation index in prediction of its broadcasting to the wearer.

In other embodiments:
  the identification step comprises a substep of selecting one or more factual episodes relating to each type of environmental event recorded during the given period using at least one selection criterion;
  a first selection criterion provides that at least one environmental measurement of the data describing each factual episode relating to each type of environmental event is compared with a reference threshold of disturbance of the quality of life;
  a second selection criterion consists of comparing a duration of each factual episode relating to each type of environmental event with a reference threshold of duration of disturbance of the quality of life;
  the identification step comprises a substep of generating an indicator of disturbance of the quality of life for each type of environmental event disturbing the quality of life identified;
  the generation substep comprises a phase of calculating the indicator of disturbance of the quality of life for each type of environmental event disturbing the quality of life identified using the following descriptive characteristics:
    a mean value of the environmental measurement or measurements included in the data describing the selected factual episodes relating to this type of environmental event;
    a total duration of the occurrence of this type of environmental event;
    the number of selected factual episodes of this type of environmental event;
    times of start and end of the selected factual episodes of this type of environmental event;
  the given period is defined automatically by the processing unit while being initiated as soon as a first factual episode of a type of environmental event is identified, and completed when a duration of exposure of the wearer to at least one type of environmental event considered to be disturbing the quality of life is higher than a reference duration threshold.

The invention also relates to a system of broadcasting, by a watch, of an informative message relating to an evaluation of the quality of life of a wearer of said watch using this method, the system comprising the following elements connected together: a processing unit, at least one environmental sensor and an interface broadcasting visual and/or audible information.

The invention also relates to a watch comprising such a system.

Advantageously, the watch is a connected mechanical watch.

The invention also relates to a computer program comprising program code instructions for executing the steps of the method when said program is executed by a processing unit.

BRIEF DESCRIPTION OF THE FIGURES

Other particularities and advantages will emerge clearly from the description that is given thereof below, by way of indication and in no way limitatively, with reference to the accompanying figures, in which.

DETAILED DESCRIPTION OF THE INVENTION

Figure 1:
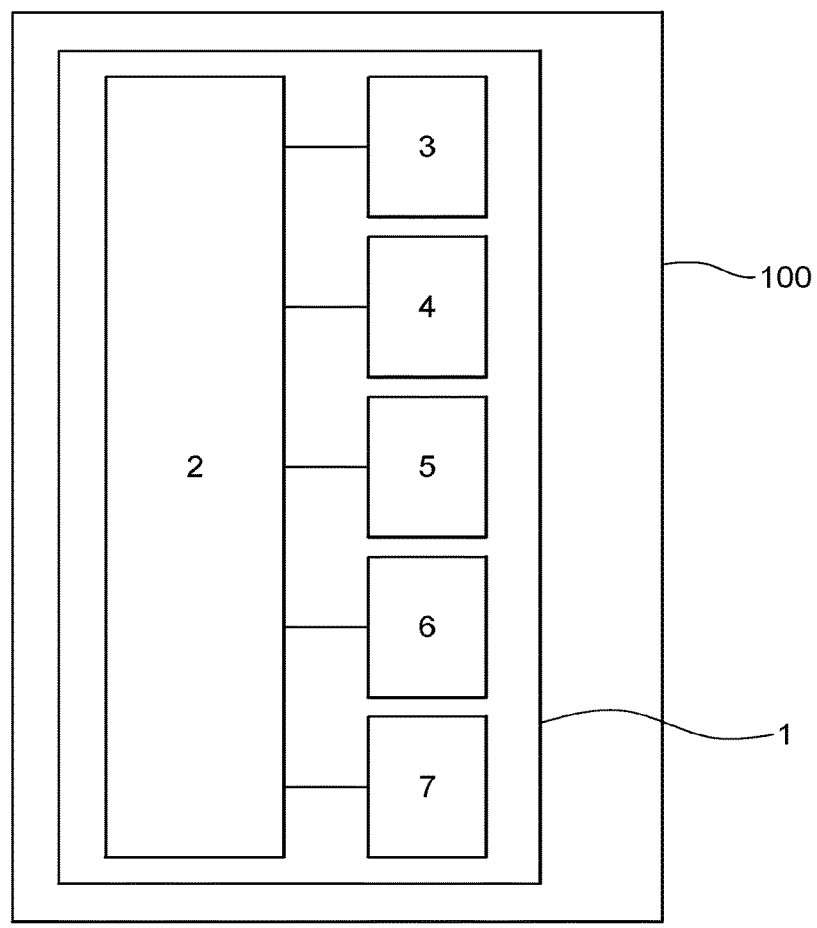
FIG. 1 is a schematic representation of a watch comprising a system for broadcasting an informative message relating to an evaluation of the quality of life of the wearer of said watch, according to one embodiment of the invention.

FIG. 1 shows a watch 100 comprising the system 1 for the broadcasting, by this watch 100, of an informative message relating to an evaluation of the quality of life of a wearer of said watch 100. Such a system 1 is included in the watch 100, which is preferably a connected mechanical watch 100 with a hybrid display. This system 1 comprises more precisely, non-limitatively and/or non-exhaustively:
- a processing unit 2 comprising hardware and software resources, in particular at least one processor cooperating with memory elements;
- an interface for broadcasting visual information 3 such as a hybrid display dial provided with a first analogue display component and a second digital and/or alphanumeric display component;
- an interface for broadcasting audible information 4 such as a loudspeaker;
- a communication interface;
- at least one environmental sensor 5;
- at least one behavioural sensor 6, and
- at least one physiological sensor 7.

In this system 1, the processing unit 2 is connected among other things to the interfaces for broadcasting visual and audible information and to the environmental 5, behavioural 6 and physiological 7 sensors.

The system 1 in this watch 100 is able to evaluate the quality of the life of the wearer preferably solely from at least one type of environmental event recorded during a given period. This type of recorded event is quantified from at least one factual episode that is particular to it and which takes place during the given period. Each factual episode is characterised by descriptive data comprising in particular one or more measurements of an environmental parameter. This environmental parameter is a quantity relating to a characteristic of the environment in which the watch 100 and the wearer thereof are present. Such a parameter, non-limitatively and/or non-exhaustively, relates to: a temperature, a relative humidity, an ambient noise level, the frequency of a continuous sound, an atmospheric pressure, an illumination, the air quality, the amount of sunlight, the lack of light, etc.

By way of example, when the parameter is a "noise level", a factual episode is defined by the following descriptive data:
- one or more measurements of this noise level are determined by at least one suitable environmental sensor 5 and transmitted to the processing unit 2;
- the duration of the occurrence of the factual episode that is calculated by the processing unit 2 is for example 10 minutes, and
- the start time 10 a.m. and the end time 10.10 a.m. determined by the processing unit 2.

It is understood that, at this stage, this environmental event relates to a "noise level", and that, for this type of event, a plurality of episodes with different descriptive data may then be estimated during the given period. Subsequently, according to the method described hereinafter, if this type of environmental event is considered to be disturbing of the quality of life of the wearer, it then becomes a "noise nuisance".

In this context, the environmental sensors 5 are specifically suitable for measuring these environmental parameters. As we shall see hereinafter, the other behavioural 6 and physiological 7 sensors participate in the making of measurements that can be used optionally by the processing unit 2 in the context of the evaluation of the quality of life of the wearer. The behavioural sensors 6 are able to measure all types of behavioural characteristics of the wearer of the watch 100 such as for example the movements or gestures made by them during the given period. To do this, these behavioural sensors 6 may comprise one or more inertial sensors of the accelerometer, gyroscope or miniature multiaxial gyrometer type such as multiaxial sensors manufactured in MEMS technology, capable of detecting angular speeds and linear accelerations along a plurality of axes associating accelerometers and/or gyroscopes. With regard to the physiological sensors 7, these are able to measure the parameters relating to the functioning of an organism of the wearer such as, for example, the pulse, blood oxygen saturation, skin impedance, blood pressure, respiratory rate, respiratory arrhythmia, skin temperature, sweating level, blood oxygen saturation or blood circulation rate.

Figure 2:
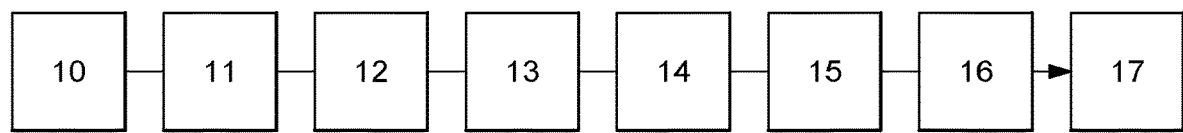
FIG. 2 is a logic diagram relating to a method for broadcasting this informative message, according to the embodiment of the invention.

Such a system 1 of the watch 100 is able to implement a method for the broadcasting by the watch 100 of this informative message shown in FIG. 2.

This method comprises a step 10 of recording, by the processing unit 2, of data describing at least one factual episode of at least one environmental event type recorded during a given period. During the step 10, from the detection of the start of the given period to the end of this period, the data describing one or more factual episodes of at least one environmental type are archived in the memory elements of the processing unit 2 of the watch 100. These data describing each factual episode comprise, non-exhaustively and non-limitatively:
- one or more environmental measurements determined by the corresponding sensors 5 and transmitted to the processing unit 2;
- the duration of the unfolding of the factual episode that is calculated by the processing unit 2, and
- the start and end times of the episode that are determined by the processing unit 2.

It is noted that the creation of an episode is related to the identification, by the processing unit 2, of a variation in an environmental parameter relating to a corresponding type of environmental event.

In this context, the period determined may be defined automatically by the processing unit while being initiated as soon as a first episode of an environmental event type is identified, and completed when the duration of exposure of the wearer to at least one type of environmental event considered to be disturbing of the quality of life is above a reference duration threshold.

Alternatively, the period determined may be predefined so that an evaluation of the quality of life is made at regular intervals, for example every 4 hours. The start of this period can then be initiated by the wearer of the watch by activating a control element, for example a push button on this watch.

The method next comprises a step 11 of identifying at least one type of environmental event disturbing the quality of life of the wearer from a processing of said descriptive data. To do this, said step 11 comprises a substep 12 of selecting one or more factual episodes relating to each type of environmental event recorded during the given period using at least one selection criterion. According to a first selection criterion, at least one environmental measurement of the data describing each factual episode relating to each type of environmental event is compared with a reference threshold of disturbance of the quality of life. If said at least one measurement is above the reference threshold of disturbance of the quality of life, then the episode can then be selected or preselected when the conditions of the selection are related to the satisfying of a second selection criterion. This second selection criterion consists of comparing the duration of each episode relating to each type of environmental event with a reference threshold of duration of disturbance of the quality of life. In this context, if the duration of the episode is above the reference threshold of duration of disturbance of the quality of life, then the episode is selected.

The identification step 11 next comprises a substep 13 of detecting one or more types of environmental event disturbing the quality of life of the wearer of the watch 100, and this from factual episodes that have been selected. This substep may make provision, for a given type of environmental event, for the number of episodes of this event to be above a reference threshold for being detected.

Subsequently, the identification step 11 comprises a substep 14 of generating an indicator of disturbance of the quality of life for each type of environmental event disturbing the quality of life detected/identified. This substep 14 comprises a phase 15 of calculating the indicator of disturbance of the quality of life for each type of environmental event disturbing the quality of life identified from descriptive characteristics. These descriptive characteristics of each type of environmental event disturbing the quality of life identified are as follows:
  a mean value of the environmental measurement or measurements included in the descriptive data of the factual episodes selected;
  the total duration of the unfolding of this type of environmental event disturbing the quality of life during the given period of the watch 100 that is equal to the sum of the durations of the factual episodes selected;
  the number of factual episodes selected;
  the start and end times of the factual episodes selected that made it possible to evaluate the effect/impact thereof on the disturbance of the cycles of the quality of life. This is because the given period comprises the succession of cycles with slow quality-of-life phases, in particular at the start of the night, which enables the body to recover physically, and the paradoxical quality of life, which corresponds to the moment when the wearer is dreaming or discharging their nervous tension.

It is noted that the calculation of the indicator of disturbance of the quality of life is carried out according to one or more of these descriptive characteristics.

Furthermore, such an identification step 11 may be performed at the end of the given period or simultaneously with the recording step 10, that is to say at the start of this given period.

The method next comprises a step 16 of estimating an index of evaluation of the quality of life as a function of the indicator of disturbance of the quality of life relating to each type of environmental event disturbing the quality of life identified. During this step 16, the processing unit 2 determines the index of evaluation of the quality of life by calculating a mean value of the indicator or indicators of disturbance of the quality of life obtained during the generation substep 14. During this calculation, coefficients can be applied to certain indicators according to the nature of the type of environmental event disturbing the quality of life to which they relate. This is because certain types of event may have a greater impact than others on the disturbance of the quality of life.

It is noted, optionally, that physiological and/or behavioural measurement data produced during the factual episodes may also be taken into account in the calculation of this index.

Next, the method comprises a step 17 of designing the informative message comprising the estimated evaluation index providing for the broadcasting thereof to the wearer. Such an informative message may be an audible message or a visual message comprising a two-dimensional or three-dimensional graphical representation comprising the index. This message may comprise, in addition to the index evaluating the quality of life, a recommendation for the attention of the wearer of the watch 100 relating to an attitude (or behaviour) to be adopted in order to improve this quality of life that is defined according to the value of this index and therefore the level of the quality of life evaluated.

It is noted that the method may also provide a step during which the wearer provides information about their evaluation of the quality of life over the day by choosing, in a contextual menu chosen in a second display component of the screen, a criterion relating to the qualification of this quality of life over the day from a list of criteria comprising for example the following mentions: a good day, a restful day, a difficult day, etc. This step next provides an archiving of this evaluation by the wearer of the watch in the form of data, the processing of which by the processing unit can make it possible to improve the precision of the evaluation of the quality of life by the present method and system.

The invention also relates to a computer program comprising program code instructions for executing steps 10 to 17 of this method when said program is executed by the processing unit 2 of the watch 100.

The invention claimed is:

1. A method for broadcasting, by a watch, an informative message relating to an evaluation of a quality of life of a wearer of said watch, the method comprising:
  recording, by processing circuitry, data describing at least one factual episode of at least one type of environmental event recorded during a given period;
  identifying a type of a disturbing environmental event that disturbs the quality of life of the wearer, from processing of the recorded data, wherein the identifying step comprises selecting one or more particular factual episodes, from the recorded data describing the at least one factual episode, each of the selected one or more particular factual episodes having corresponding measurement data that exceeds a first threshold and a corresponding time duration that exceeds a second threshold;
  estimating an evaluation index of the quality of life of the wearer from an indicator of a level of disturbance of the quality of life that is calculated for the identified type of the disturbing environmental event; and
  generating the informative message comprising the estimated evaluation index and broadcasting the informative message to the wearer.

2. The method according to claim 1, wherein the identifying step further comprises generating the indicator of the level of disturbance of the quality of life from the selected one or more particular factual episodes.

3. The method according to claim 2, wherein the generating step comprises calculating the indicator of the level of the disturbance of the quality of life for the identified type of disturbing environmental event that disturbs the quality of life based on:
- a mean value of the environmental measurement data included in the recorded data describing the selected one or more particular factual episodes relating to the identified type of disturbing environmental event;
- a total duration of the occurrence of the identified type of disturbing environmental event;
- a number of the selected one or more particular factual episodes of the identified type of disturbing environmental event; and
- times of start and end of the selected one or more particular factual episodes of the identified type of disturbing environmental event.

4. The method according to claim 1, wherein the given period is defined automatically by the processing circuitry while being initiated, as soon as a first factual episode of the at least one factual episode is identified, and completed when a duration of exposure of the wearer to the identified type of disturbing environmental event that disturbs the quality of life is higher than a reference duration threshold.

5. A system of broadcasting, by a watch, of the informative message relating to the evaluation of the quality of life of the wearer of said watch using the method according to claim 1, the system comprising:
- the processing circuitry;
- at least one environmental sensor; and
- an interface configured to broadcast at least one of visual information and audible information.

6. The watch comprising the system according to claim 5.

7. The watch according to claim 6, wherein the watch is a connected mechanical watch.

8. A non-transitory computer-readable storage medium storing a computer program comprising program code instructions that when executed, cause the processing circuitry to execute the method according to claim 1.

9. The method of claim 1, wherein the estimating step comprises estimating the evaluation index by calculating a mean value of the indicator for a plurality of types of disturbing environmental events that disturb the quality of life of the wearer.

* * * * *